(12) United States Patent
Hwang et al.

(10) Patent No.: US 7,485,452 B2
(45) Date of Patent: Feb. 3, 2009

(54) METHOD OF MAKING OPTICALLY ACTIVE ESTER DERIVATIVES AND THEIR ACIDS FROM RACEMIC ESTERS

(75) Inventors: Soon Ook Hwang, Daejeon (KR); Sun Ho Chung, Daejeon (KR)

(73) Assignee: EnzyTech, Ltd., Daejeon (KR)

( * ) Notice: Subject to any disclaimer, the term of this patent is extended or adjusted under 35 U.S.C. 154(b) by 91 days.

(21) Appl. No.: 11/587,228

(22) PCT Filed: Apr. 27, 2005

(86) PCT No.: PCT/KR2005/001213

§ 371 (c)(1),
(2), (4) Date: Oct. 23, 2006

(87) PCT Pub. No.: WO2005/111227

PCT Pub. Date: Nov. 24, 2005

(65) Prior Publication Data

US 2008/0038802 A1 Feb. 14, 2008

(30) Foreign Application Priority Data

Apr. 29, 2004 (KR) ............... 10-2004-0029791

(51) Int. Cl.
*C12P 41/00* (2006.01)
(52) U.S. Cl. .................................. 435/280
(58) Field of Classification Search ............ None
See application file for complete search history.

(56) References Cited

U.S. PATENT DOCUMENTS

| 4,957,867 A | 9/1990 | Minai et al. |
| 5,108,916 A | 4/1992 | Cobbs et al. |

FOREIGN PATENT DOCUMENTS

| EP | 1 408 107 A3 | 5/2006 |
| KR | 1020000059531 A | 10/2000 |

OTHER PUBLICATIONS

Sharma et al, Journal of Molecular Catalysis B: Enzymatic, Enantio-reversal in Candida rugosa Lipase-catalyzed Esterification of 3-Hydroxybutyric Acid, 2000, 10, pp. 531-534.*

Zhou et al., Stereochemical Control of Yeast Reductions. 1. Asymmetric Synthesis of L-Carnitine, J. Am. Chem. Soc., 1983, 105, pp. 5925-5926.
Shiosaki et al., Phosphorus-Containing Inhibitors of HMG-CoA Reductase. 1. 4-[(2-Arylethyl)hydroxyphosphinyl]-3-hydroxybutanoic Acids: A New Class of Cell-Selective Inhibitors of Cholesterol Biosynthesis, J. Med. Chem. 1990, 33, pp. 2952-2956.
Noyori et al., Asymmetric Hydrogenation of β-Keto Carboxylic Esters. A Practical, Purely Chemical Access to β-Hydroxy Esters in High Enantiomeric Purity, J. Am. Chem. Soc., 1987, 109, pp. 5856-5858.
Jayasinghe et al., The Yeast Medicated Reduction of Ethyl acetoacetate in Petroleum Ether, Tetrahedron Letters, 1993, vol. 34, No. 24, pp. 3849-3850.
Medson et al., The stereoselective preparation of β-hydroxy esters using a yeast reduction in an organic solvent, Tetrahedron: Asymmetry, 1997, vol. 8, No. 7, pp. 1049-1054.
Chin-Joe et al., Hydrolytic Activity in Baker's Yeast Limits the Yield of Asymmetric 3-Oxo Ester Reduction, Biotechnology and Bioengineering, 2000, vol. 69, No. 4, pp. 370-376.
Sugai et al., Enzymatic Preparation of Ethyl (S)-3-Hydroxybutanoate with a High Enantiomeric Excess, Agric. Biol. Chem, 1989, 53 (7), pp. 2009-2010.
Fishman et al., A Two-Step Enzymatic Resolution Process for Large-Scale Production of (S)- and (R)-Ethyl-3-Hydroxybutyrate, Biotechnology and Bioengineering, 2001, vol. 74, No. 3, pp. 256-263.
Lee et al., Preparation of alkyl (R)-(-)-3-hydroxybutyrate by acidic alcoholysis of poly-(R)-(-)-3-hydroxybutyrate, Enzyme and Microbial Technology 27, 2000, pp. 33-36.

(Continued)

*Primary Examiner*—Paul A Zucker
(74) *Attorney, Agent, or Firm*—John W. Renner; Renner, Otto, Boisselle & Sklar

(57) ABSTRACT

The present invention relates to process for the preparing of optically active ester derivatives and their acid derivatives which are used intensively as important chiral intermediates from racemic β-hydroxybutyl ester derivatives. In more detail, this invention relates to the process for preparing optically active β-hydroxybutyl ester derivatives and their acid derivatives by stereospecific hydrolysis of racemic β-hydroxybutyl ester derivatives using Upases or lipase-producing microorganisms in the aqueous phase or organic phase including aqueous solvent. The method of making optically active ester derivatives and their acid derivatives by hydrolysis of β-hydroxybutyl ester derivatives represented by the general formula 1 in scheme 1 is easier and more economical comparing to the conventional methods and the products have high optical purity. Also separation of ester derivatives from acid derivatives is easy after reaction. Thus this method is a useful process on the industrial scale.

2 Claims, No Drawings

OTHER PUBLICATIONS

Yamamoto et al., Synthesis of Ethyl (R)-4-Chloro-3-hydroxybutanoate with Recombinant *Escherichia coli* Cells Expressing (S)-Specific Secondary Alcohol Dehydrogenase, Biosci. Biotechnol. Biochem., 2002, 66 (2), pp. 481-483.

Hoff et al., Lipase-catalyzed resolution of esters of 4-chloro-3-hydroxybutanoic acid: effects of the alkoxy group and solvent on the enantiomeric ratio, Tetrahedron: Asymmetry 10, 1999, pp. 1401-1412.

Suzuki et al., Dual production of highly pure methyl (R)-4-chloro-3-hydroxybutyrate and (S)-3-hydroxy-γ-butyrolactone with Enterobacter Sp., Enzyme and Microbial Technology 24, 1999, pp. 13-20.

Bucciarelli et al., Enantioselective lipase-catalyzed acetylation of β-lactam precursors of carbapenem antibiotics, J. Chem. Soc., Perkin Trans. 1, 1999, pp. 2489-2494.

Kataoka et al., Stereoselective reduction of ethyl 4-chloro-3-oxobutanoate by *Escherichia coli* transformant cells coexpressing the aldehyde reductase and glucose dehydrogenase genes, Appl. Microbiol Biotechnol, 51, 1999, pp. 486-490.

Boaz, Neil W., Enzymatic Hydrolysis of Ethyl 3-Hydroxy-3-phenylpropanoate: Observations on an Enzyme Active-Site Model, J. Org. Chem. 57, 1992, pp. 4289-4292.

* cited by examiner

METHOD OF MAKING OPTICALLY ACTIVE ESTER DERIVATIVES AND THEIR ACIDS FROM RACEMIC ESTERS

TECHNICAL FIELD

The present invention relates to a process for the preparation of optically active β-hydroxybutyl ester derivatives and their acid derivatives. In more detail, this invention relates to the process for preparing optically active α-hydroxybutyl ester derivatives and their acid derivatives by the hydrolysis of racemic α-hydroxybutyl ester derivatives represented by the general formula 1 in scheme 1 using lipases or lipase-producing microorganisms.

The above-mentioned optically active α-hydroxybutyl ester derivatives and their acid derivatives can be used intensively as important chiral intermediates. Also, α-hydroxybutyl ester derivatives and their acid derivatives produced by this invention have high optical purity and this method can be used in practical process because separation and recovery of the products are easy. Therefore this invention can be used on the industrial scale.

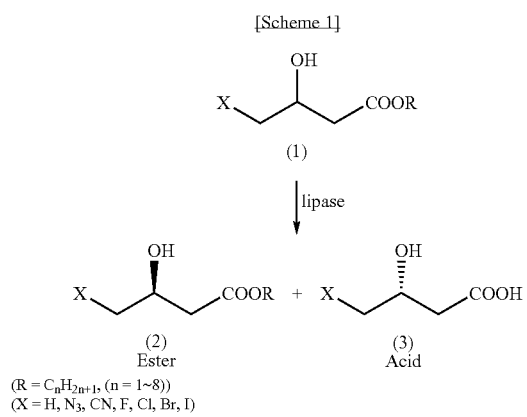

[Scheme 1]

(R = $C_nH_{2n+1}$, (n = 1~8))
(X = H, $N_3$, CN, F, Cl, Br, I)

According to a report, ethyl (R)-3-hydroxybutyrate is an intermediate for an anti-glaucoma drug (Chirality in industry II. Chichester, UK:Wiley, 1997, 245-262) and (S)-3-hydroxybutyrate is used for synthesizing pheromones (Tertahedron, 1989, 45:3233-3298) and carbapenems (Journal of the Chemical Society. Perkin Transaction, 1999, 1: 2489-2494).

And ethyl (R)-4-chloro-3-hydroxybutyrate is used for synthesizing L-carnitine(Journal of the American Chemical Society, 1983, 105:5925-5926), (R)-4-amino-3-hydroxybutyric acid (GABOB) and (R)-hydroxy-2-pyrrolidone. Ethyl (S)-4-chloro-3-hydroxybutyrate is a valuable synthon for the production of hydroxyymethylglutaryl CoA (HMG-CoA) reductase inhibitor (Journal of Medicinal Chemistry, 1990, 33:2952-2956).

BACKGROUND ART

There are several methods to prepare optically active β-hydroxybutyl ester derivatives. Ethyl (S)-3-hydroxybutyrate is synthesized by asymmetric hydrogenation of ethylacetoacetate using BINAP-coordinated Ru(II) complexes (Journal of the American Chemical Society, 1987, 109:5856-5858). However, this method has disadvantages of high pressure during the reaction and high cost of metal catalyst.

Another method is the reduction of 3-oxo-esters using microorganisms. Jayasinghe et al. (Tetrahedron Letters, 1993, 34:3949-3950) obtained ethyl (S)-3-hydroxybutyrate (58% yield, 94% e.e) by the reduction of ethyl acetoacetate using freeze-dried yeast in petroleum ether and Medson et al.(Tetrahedron:Asymmetry, 1997, 8:1049-1054) obtained ethyl (S)-3-hydroxybutyrate (yield 69%, 99% e.e) from ethyl acetoacetate by the reduction using yeast in organic solvent. Chin-Joe et al.(Biotechnology and Bioengineering, 2000, 69:370-376) obtained ethyl (S)-3-hydroxybutyrate (99% e.e) at 85% conversion by the reduction of ethyl acetoacetate using Baker's yeast. However, these methods have disadvantages of low yield and purification problem after reaction.

On the other hand, Sugai et al.(Agricultural and Biological Chemistry, 1989, 53:2009-2010) obtained ethyl (S)-3-hydroxybutyrate (99.4% e.e) by transesterification of racemic ethyl 3-hydroxybutyrate using vinyl butanoate as an acylating agent and porcine pancreatic lipase as a catalyst. Fishman et al.(Biotechnology and Bioengineering, 2001, 74:256-263) obtained ethyl (S)-3-hydroxybutyrate (40% yield, 99.4% e.e) using CALB (*Candida antartica*) lipaseand vinyl acetate as an acyl donor.

In another case, ethyl (R)-3-hydroxybutyrate can be prepared by acidic alcoholysis of Poly-(R)-3-hydroxybutyrate accumulated by microorganisms (Enzyme and Microbial Technology, 2000, 27:33-36).

Optically active ethyl 4-chloro-3-hydroxybutyrate can be produced by reduction of ethyl 4-chloroacetoacetate. Matsuyama et al.(Japan Kokai Tokkyo Koho, 06-209782, Aug. 2, 1994) obtained ethyl (S)-4-chloro-3-hydroxybutyrate (97% yield, 98% e.e) using *Kluyveromyces lactis* NRIC 1329. Kataoka et al.(Applied microbiology and Biotechnology, 1999, 51:486-490) obtained ethyl (R)-4-chloro-3-hydroxybutyrate (94% yield, 92% e.e) using recombinant microorganism, which coexpress both the alcohol reductase Igene from *Sporobolomyces salmonicolor* and the glucose dehydrogenase gene from *Bacillus megaterium*. Yamamoto et al. (Bioscience Biotechnology and Biochemistry, 2002, 66(2): 481-483) produced ethyl (R)-4-chloro-3-hydroxybutyrate (95.2% conversion, 99% e.e) using recombinant microorganism expressing secondary alcohol dehydrogenase from *Candida parapsilosis*. However, these methods have disadvantage of long reaction time.

On the other hand, Hoff et al.(Tetrahedron:Asymmetry, 1999, 10:1401-1412) obtained ethyl (S)-4-chlro-3-hydroxybutyrate (24% yield, 86% e.e) by transesterifying for 5 days using *Rhizomucor miehei* lipase (RML) in organic phase (benzene).

Suzuki et al.(Enzyme Microbiology and Technology, 1999, 24:13-20) produced ethyl (R)-4-chloro-3-hydroxybutyrate (99.8% e.e) using dechlorinase-producing microorganism.

As previously stated, optically active β-hydroxybutyl ester derivatives can be prepared by the stereoselective reduction of keto esters or the enzymatic transesterification. However, these methods are not suitable due to their disadvantages including low enantiomeric excess, low yield or difficulties in the separation of products and reactants after reaction. For solving these problems, there is hydrolysis of α-hydroxybutyl ester derivatives. Santaniello et al.(Gazzetta Chemica Italiana, 1989, 119:581-584) obtained ethyl (R)-4-chloro-3-hydroxybutyrate and (S)-their acid by hyrolysis of ethyl 4-chloro-3-hydroxybutyrate using pig liver esterase. However, this method has disadvantages of low yield (23%) and low enantiomeric excess (16% e.e) and is not suitable for industrial use.

DISCLOSURE OF INVENTION

Technical Problem

The process for preparing of β-hydroxybutyl ester derivatives and their acid derivatives of high optical purity was developed from racemic β-hydroxybutyl ester derivatives represented by the general formula 1 in scheme 1 by stereospecific hydrolysis using lipases or lipase-producing microorganisms.

This method is simple and ester derivatives and their acid derivatives of higher optical purity can be obtained comparing to the conventional methods.

Accordingly, the objective of this invention is to provide the method of preparing optically active esters and their acids from racemic β-hydroxybutyl ester derivatives using enzymes or microorganisms.

For the above objectives, the present invention consists of the process for preparing high optically active β-hydroxybutyl ester derivatives and their acids from racemic β-hydroxybutyl ester derivatives by stereospecific hydrolysis using lipases or lipase-producing microorganisms as biocatalysts in aqueous phase or organic phase including aqueous solvent.

Technical Solution

This invention is explained in more detail as follows. As mentioned above, this invention relates to the process for preparing optically active β-hydroxybutyl ester derivatives and their acid derivatives by stereospecific hydrolysis of racemic β-hydroxybutyl ester derivatives using lipases or lipase-producing microorganisms as biocatalysts in aqueous phase or organic phase including aqueous solvent.

In this invention, methyl 3-hydroxybutyrate, ethyl 3-hydroxybutyrate, butyl 3-hydroxybutyrate, ethyl 3-azido-3-hydroxybutyrate, ethyl 4-chloro-3-hydroxybutyrate, ethyl 4-bromo-3-hydroxybutyrate and ethyl 4-cyano-3-hydroxybutyrate are used as racemic β-hydroxybutyl esters, but the reactant is not restricted to them. In the general formula 1 in scheme 1, X is H, CN, $N_3$, F, Cl, Br or I and R is $C_nH2_{n+1}$ (n=1~8).

Non-limiting examples of the commercially available lipases include PS lipase from Amano Inc., *Candida rugosa* lipase and Novozyme 435 and non-limiting examples of the lipase-producing microorganism include *Candida rugosa* and *Rhodococcus butanica*.

After reaction, optically active esters and their acids are separated respectively by solvent extraction method or column chromatography.

In this invention, racemic compounds were determined by gas chromatography (Donam Instrument Inc. Model 6200) equipped with HP-FFAP (Agilent, Inc., 30 mm×0.53 m) column. The oven temperature was maintained initially at 70° C. for 5 min and then raised at the rate of 10° C./min to 220° C., and maintained for 10 minutes. Helium gas is used as carrier at the rate of 2 ml/min, and compounds were detected using FID detector. The typical retention time of the components in this invention were as follows:

racemic methyl 3-hydroxybutyrate-15.48 min
racemic ethyl 3-hydroxybutyrate-14.32 min
racemic butyl 3-hydroxybutyrate-17.16 min
racemic ethyl 4-azido-3-hydroxybutyrate-22.50 min
racemic ethyl 4-chloro-3-hydroxybutyrate-20.31 min Racemic ethyl 4-bromo-3-hydroxybutyrate and racemic ethyl 4-cyano-3-hydroxybutyrate were analyzed using the same method used in the analysis of racemic methyl 3-hydroxybutyrate except that oven temperature was increased at 20° C./min. In this condition racemic ethyl 4-bromo-3-hydroxybutyrate and racemic ethyl 4-cyano-3-hydroxybutyrate are detected at 11.7 min and 14.07 min respectively.

Optically active methyl 3-hydroxybutyrate, ethyl 3-hydroxybutyrate, butyl 3-hydroxybutyrate and ethyl 4-azido-3-hydroxybutyrate were determined by HPLC (Waters, Inc., Model 1525) equipped with chial column OD-H (Daicel, 0.46 cm×25 cm) using hexane and isopropyl alcohol mixture (90:10) as mobile phase. The absorbance was 220 nm and flow rate was 0.7 ml/min. The typical retention time of the components in this invention was as follows:

methyl (R)-3-hydroxybutyrate-10.28 min
methyl (S)-3-hydroxybutyrate-12.44 min
ethyl (R)-3-hydroxybutyrate-12.77 min
ethyl (S)-3-hydroxybutyrate-11.43 min
butyl (R)-3-hydroxybutyrate-9.4 min
butyl (S)-3-hydroxybutyrate-10.64 min
ethyl (R)-4-azido-3-hydroxybutyrate-8.7 min
ethyl (S)-4-azido-3-hydroxybutyrate-10.86 min Optically active ethyl 4-cyano-3-hydroxybutyrate was determined by a gas chromatography(Donam Instrument Inc. Model 6200) equipped with chiral column G-TA(Astec, 30 mm×0.32 m). The oven temperature was maintained initially at 100° C. for 5 min and then raised to 170° C. at the rate of 10° C./min, and maintained for 20 minutes. Helium gas was used as carrier gas and column head pressure was maintained at 10 psi, and compounds were detected using FID detector. In this condition, the typical retention time of ethyl (R)-4-cyano-3-hydroxybutyrate and ethyl (S)-4-cyano-3-hydroxybutyrate was 16.75 min and 16.53 min respectively.

Optically active ethyl 4-chloro-3-hydroxybutyrate was determined by a HPLC (Lab Alliance, Model 201) equipped with chial column OB-H (Daicel, 0.46 cm×25 cm) using hexane and isopropyl alcohol mixture (95:5) as mobile phase. The flow rate was 0.7 ml/min and absorbance was 215 nm. The typical retention time of ethyl (R)-4-chloro-3-hydroxybutyrate and ethyl (S)-4-chloro-3-hydroxybutyrate was 14.42 min and 15.38 min, respectively.

Optically active ethyl 4-bromo-3-hydroxybutyrate was determined by a HPLC (Lab Alliance, Model 201) equipped with chial column AD-H(Daicel, 0.46 cm×25 cm) using hexane and isopropyl alcohol mixture (90:10) as mobile phase. The flow rate was 0.7 ml/min and absorbance was 220 nm. In this condition, the typical retention time of ethyl (R)-4-bromo-3-hydroxybutyrate and ethyl (S)-4-bromo-3-hydroxybutyrate was 12.23 min and 11.24 min, respectively.

And racemic compounds were confirmed by FT-NMR (Burker, Model DRX300 or JEOL, Model AR400) and the results are as follows:

ethyl 4-azido-3-hydroxybutyrate:
$^1$H-NMR (CDCl$_3$, 300 MHz) δ(ppm)=1.28 (t, 3H), 2.53 (m, 2H), 3.28 (d, 1H), 3.34 (m, 2H), 4.21 (q, 2H)

ethyl 4-chloro-3-hydroxybutyrate:
$^1$H-NMR (CDCl$_3$, 400 MHz) δ(ppm)=1.28 (t, 3H), 2.62 (d, 2H), 3.53 (br, 1H), 3.60 (d, 2H), 4.20 (q, 2H), 4.33 (m, 1H)

ethyl 4-bromo-3-hydroxybutyrate:
$^1$H-NMR (CDCl$_3$, 400 MHz) δ(ppm)=1.28 (t, 3H), 2.7 (m, 2H), 3.48 (dd, 1H), 3.51 (dd, 1H), 4.17 (q, 2H), 4.20 (m, 1H)

ethyl 4-cyano-3-hydroxybutyrate:
$^1$H-NMR (CDCl$_3$, 300 MHz) δ(ppm)=1.26 (t, 3H), 2.5~2.7 (m, 4H), 4.18 (q, 2H), 4.32 (m, 1H)

A better understanding of the present invention may be obtained through the following examples which are set forth to illustrate, but are not to be construed as the limit of the present invention.

EXAMPLE 1

Racemic ethyl 3-hydroxybutyrate (1%, v/v) was added to the vial containing 5 ml potassium phosphate buffer (pH 8.0, 0.1 M) and Novozyme 435 (4%, w/v). The reaction was carried out at 30° C. for 2 hours. The reaction mixture was extracted with ethyl acetate and analyzed by above-mentioned method. Ethyl (S)-3-hydroxybutyrate (97% e.e) was obtained from organic solvent at 55% conversion. The aqueous solution was acidified with hydrochloric acid and extracted with organic solvent. After esterification, ethyl (R)-3-hydroxybutyrate with optical purity of 80.4% e.e was obtained.

EXAMPLES 2-3

Instead of lipase used in Example 1, whole cells (20% (w/v)) were used. Lipase-producing microorganisms were isolated by cultivating in a medium containing 1% tributyrin. Isolated strains assimilated tributyrin and made clear zone. The strains were grown in LB medium or GYP medium including glucose, and microorganisms were harvested by centrifuge and used as biocatalysts. The results are shown in Table 1.

TABLE 1

| Example | Microorgnism | Reaction time(hr) | Conversion (%) | % e.e for ester | Configuration |
|---|---|---|---|---|---|
| 2 | Candida rugosa KCCM 50521 | 62 | 69.6 | 99 | S |
| 3 | Rhodococcus butanica ATCC 21197 | 3.5 | 63.9 | 99 | S |

EXAMPLES 4-5

Instead of ethyl 3-hydroxybutyrate used in Example 1, 1% methyl 3-hydroxybutyrate and 5% butyl 3-hydroxybutyrate were used as reactants. The reaction was carried out with novozyme 435 lipase and the results are shown in Table 2.

TABLE 2

| Example | Reactant | Reaction time(hr) | Conversion (%) | % e.e for ester | Configuration |
|---|---|---|---|---|---|
| 4 | methyl 3-hydroxybutyrate | 5 | 78.0 | 98.8 | S |
| 5 | butyl 3-hydroxybutyrate | 6 | 82.0 | 78.5 | S |

EXAMPLE 6

Instead of ethyl 3-hydroxybutyrate used in Example 1, ethyl 4-azido-3-hydroxybutyrate was used. The reaction was carried out for 1 hour and ethyl (S)-4-azido-3-hydroxybutyrate (80.2% e.e) was obtained at 83.5% conversion.

EXAMPLES 7-8

Instead of ethyl 3-hydroxybutyrate used in Example 1, ethyl 4-chloro-3-hydroxybutyrate was used as a reactant and lipases were used as biocatalysts. The results are shown in Table 3.

TABLE 3

| Example | Lipase | Reaction time(hr) | Conversion (%) | % e.e for ester | Configuration |
|---|---|---|---|---|---|
| 7 | Pseudomonas cepatia lipase | 22 | 71.0 | 99 | S |
| 8 | Candida rugosa lipase | 32 | 76.0 | 99 | R |

EXAMPLE 9

Instead of ethyl 3-hydroxybutyrate used in Example 1, ethyl 4-bromo-3-hydroxybutyrate (1%, w/v) was used as a reactant and novozyme 435 lipase was used as a biocatalyst. After reaction for 1 hour 40 minutes, ethyl (R)-4-bromo-3-hydroxybutyrate (99% e.e) was obtained at 88.3% conversion.

EXAMPLE 10

Instead of ethyl 3-hydroxybutyrate used in Example 1, ethyl 4-cyano-3-hydroxybutyrate (1%, w/v) was used as a reactant and novozyme 435 lipase was used as a biocatalyst. After reaction for 3 hours, ethyl (R)-4-cyano-3-hydroxybutyrate (99% e.e) was obtained at 57.3% conversion.

EXAMPLES 11-13

Instead of ethyl 3-hydroxybutyrate used in Example 2, ethyl 4-chloro-3-hydroxybutyrate was used as a reactant and microorganisms in Table 4 were used as biocatalysts. The results are shown in Table 4.

TABLE 4

| Example | Microorganism | Reaction time (hr) | Conversion (%) | % e.e for ester | Configuration |
|---|---|---|---|---|---|
| 11 | Candida rugosa KCTC 7292 | 32 | 76.1 | 99 | S |
| 12 | Candida rugosa KCCM 50521 | 47 | 77.3 | 99 | S |
| 13 | Rhodococcus butanica ATCC 21197 | 8 | 76.1 | 99 | R |

INDUSTRIAL APPLICABILITY

In accordance with Examples 1-13, optically active β-hydroxybutyl ester derivatives can be produced easily by hydrolysis of this invention. With appropriate lipases or microorganisms, β-hydroxybutyl ester derivatives of high optical purity can be produced. Also, it is easy to separate optically active esters from their acids after reaction. Therefore, this method is a useful process on the industrial scale.

The invention claim is:

1. A process for preparing optically active β-hydroxybutyl ester derivatives and their acids derivatives from a racemic β-hydroxybutyl ester derivative, the process comprising reacting a mixture of a racemic β-hydroxybutyl ester derivative of the formula (1)

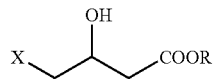
(1)

and a lipase or lipase-producing microorganism as a biocatalyst, the reaction being carried out in the aqueous phase or organic phase including aqueous solvent and providing a β-hydroxybutyl ester derivative of the formula (2) and a β-hydroxybutyl acid derivative of the formula (3),

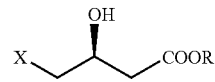
(2)

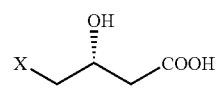
(3)

wherein R is $C_nH2_{n+1}$, (n=1~8) and X is H, $N_3$, CN, F, Cl, Br or I.

2. A process according to claim 1, wherein the reaction mixture comprises a lipase-producing microorganism selected from *Candida rugosa* KCTC 7292, *Candida rugosa* KCCM 5521, or *Rhodococcus butanica* ATCC 21197.

* * * * *